(12) United States Patent
Chow et al.

(10) Patent No.: US 6,793,725 B2
(45) Date of Patent: Sep. 21, 2004

(54) PREMIXED CALCIUM PHOSPHATE CEMENT PASTES

(75) Inventors: Laurence C. Chow, Germantown, MD (US); Shozo Takagi, Gaithersburg, MD (US)

(73) Assignee: ADA Foundation, Chicago, IL (US)

(*) Notice: Subject to any disclaimer, the term of this patent is extended or adjusted under 35 U.S.C. 154(b) by 46 days.

(21) Appl. No.: 10/057,554

(22) Filed: Jan. 23, 2002

(65) Prior Publication Data

US 2002/0137812 A1 Sep. 26, 2002

Related U.S. Application Data

(60) Provisional application No. 60/263,894, filed on Jan. 24, 2001.

(51) Int. Cl.$^7$ .............................. C04B 12/02; C09K 3/00
(52) U.S. Cl. .......................... 106/35; 106/690; 106/691
(58) Field of Search ........................... 106/35, 690, 691

(56) References Cited

U.S. PATENT DOCUMENTS

| | | | |
|---|---|---|---|
| 3,679,360 A | 7/1972 | Rubin et al. | |
| 3,787,900 A | 1/1974 | McGee | |
| 3,913,229 A | 10/1975 | Driskell et al. | |
| 3,929,971 A | 12/1975 | Roy | |
| 4,097,935 A | 7/1978 | Jarcho | |
| 4,486,403 A | 12/1984 | Mechanic et al. | |
| 4,497,075 A | 2/1985 | Niwa et al. | |
| 4,512,038 A | 4/1985 | Alexander et al. | |
| 4,518,430 A | 5/1985 | Brown et al. | |
| 4,599,085 A | 7/1986 | Riess et al. | |
| 4,612,053 A | 9/1986 | Brown et al. | |
| 4,655,777 A | 4/1987 | Dunn et al. | |
| 4,880,610 A | 11/1989 | Constantz et al. | |
| 4,897,250 A | 1/1990 | Sumita | |
| RE33,161 E | 2/1990 | Brown et al. | |
| RE33,221 E | 5/1990 | Brown et al. | |
| 4,963,151 A | 10/1990 | Ducheyne et al. | |
| 5,034,059 A | 7/1991 | Constantz et al. | |
| 5,037,639 A | 8/1991 | Tung | |
| 5,047,031 A | 9/1991 | Constantz et al. | |
| 5,053,212 A | 10/1991 | Constantz et al. | |
| 5,092,888 A | 3/1992 | Iwamoto et al. | |
| 5,129,905 A | 7/1992 | Constantz et al. | |
| 5,181,930 A | 1/1993 | Dumbleton et al. | |
| 5,192,330 A | 3/1993 | Chang et al. | |
| 5,236,456 A | 8/1993 | O'Leary et al. | |
| 5,238,491 A | 8/1993 | Sugihara et al. | |
| 5,336,264 A | 8/1994 | Constanz et al. | |
| 5,455,231 A | 10/1995 | Constantz et al. | |
| 5,496,399 A | 3/1996 | Ison et al. | |
| 5,522,893 A | 6/1996 | Chow et al. | |
| 5,525,148 A | 6/1996 | Chow et al. | |
| 5,542,973 A | 8/1996 | Chow et al. | |
| 5,545,254 A | 8/1996 | Chow et al. | |
| 5,556,687 A | 9/1996 | McMillin | |
| 5,652,056 A | 7/1997 | Pepin | |
| 5,695,729 A | 12/1997 | Chow et al. | |
| 5,721,049 A | 2/1998 | Marcolongo et al. | |
| 5,766,618 A | 6/1998 | Laurencin et al. | |
| 5,782,971 A | 7/1998 | Constantz et al. | |
| 5,962,028 A | 10/1999 | Constantz | |
| 5,976,234 A | 11/1999 | Chow et al. | |
| 5,997,624 A | 12/1999 | Chow et al. | |
| 6,077,989 A | 6/2000 | Kandel et al. | |
| 6,136,029 A | 10/2000 | Johnson et al. | |
| 6,207,098 B1 | 3/2001 | Nakanishi et al. | |
| 6,214,008 B1 | 4/2001 | Illi | |
| 6,281,256 B1 | 8/2001 | Harris et al. | |
| 6,281,257 B1 | 8/2001 | Ma et al. | |
| 6,287,341 B1 | 9/2001 | Lee et al. | |
| 6,325,992 B1 | 12/2001 | Chow et al. | |

FOREIGN PATENT DOCUMENTS

| | | |
|---|---|---|
| DE | 4016135 A1 | 11/1999 |
| EP | 041676 A1 | 3/1991 |
| EP | 0520 690 A2 | 12/1992 |
| WO | WO 9503369 | 2/1995 |

OTHER PUBLICATIONS

Briner, et al., "Significance of Enamel Remineralization", *J. Dent. Res.* 53:239–243 (1974), no month.

Silverstone, "Remineralization Phenomena", *Caries Res.* 11(Supp. 1): 59–84, (1977), no month.

Brown, Solubilities of Phosphates and Other Sparingly Soluble Compounds, from Griffith, et al., *Environmental Phosphorous Handbook* (John Wiley & Sons, New York 1973), no month.

Miyazaki, et al., "An Infrared Spectroscopic Study of Cement Formation of Polymeric Calcium Phosphate Cement," *Journal of Japanese Society for Dental Materials and Devices*, vol. 11, No. 2, 1992, no month, considered to extent of abstract.

Brown, et al., "Crystallography of Tetracalcium Phosphate," *J. Res. Nat. Bur. Stands.* 69A: 547–551) (1965), no month.

Driskell, et al., "Development of Ceramic and Ceramic Composite Devices for Maxillofacial Application", *J. Biomed. Mat. Res.* 6: 345–361 (1972), no month.

Gelhard et al, "Rehardening of Artificial Enamel Lesions in Vivo", *Caries Res.* 13: 80–83 (1979), no month.

Gregory, et al., "Solubility of $CaHPO_4 2H_2O$ in the System $Ca(OH)_2$—$H_3PO_4$—$H_2O$ at 5, 15, 25, and 37.5 ° C.," *J. Res. Nat. Bur. Stand,* 74A: 461–475 (1970), no month.

Gregory, et al., "Solubility of —$Ca_3(PO_4)_2$ in the System $Ca(OH)_2$—$H_3PO_4$—$H_2O$ at 5, 15, 25 and 37° C.," *J. Res. Nat. Bur. Stand.* 78A: 667–674 (1974), no month.

Levine, "Remineralization of Natural Carious Lesions of Enamel in vitro," *Brit. Dent. J.,* 137: 132–134 (1974), no month.

(List continued on next page.)

Primary Examiner—Elizabeth D. Wood
(74) Attorney, Agent, or Firm—Banner & Witcoff, Ltd.

(57) ABSTRACT

A bone or dental implant material in the form of a paste includes a mixture of calcium phosphate powders, that are capable of forming hydroxyapatite, with liquid glycerol and hydroxypropyl methylcellulose and $Na_2HPO_4$. The paste will harden upon exposure to water with the time to harden controlled by the choice and ratio of constituents.

10 Claims, No Drawings

OTHER PUBLICATIONS

McDowell, et al., "Solubility of —$Ca_5(PO_4)_3$ in the System $Ca(OH)_2$—$H_3PO_4$—$H_2O$ at 5, 15, 25 and 37° C.," *J. Res. Nat. Bur. Stand.* 81A:273–281 (1977), no month.

McDowell, et al., "Solubility Study of Calcium Hydrogen Phosphate. Ion Pair Formation," *Inorg. Chem.* 10:1638–1643 (1971), no month.

Moreno, et al., "Stability of Dicalcium Phosphate Dihydrate in Aqueous Solutions and Solubility of Octacalcium Phosphate," *Soil Sci. Soc. Am. Proc.* 21: 99–102 (1960), no month.

Patel, et al., "Solubility of $CaHPO_4$ $2H_2O$ in the Quaternary System $Ca(OH)_2$—$H_3PO_4$—$NaCl$—$H_2O$ at 25° C.," *J. Res. Nat. Bur. Stands.* 78A: 675–681 (1974), no month.

Pickel, et al. "The Effect of a Chewing Gum Containing Dicalcium Phosphate on Salivary Calcium and Phosphate", *Ala. J. Med. Sci.* 2: 286–287, No Date.

Zimmerman, et. al., "The Effect of Remineralization Fluids on Carious Lesions in Vitro," IADR Abstract No. 282 (1979), no month.

*Guide to Dental Materials and Devices*, 7th Ed. (ADA 1974) pp. 49–64, no month.

Brown, et al., (1988): "A New Calcium Phosphate, Water Setting Cement," *Cements Research Progress* 1986, P.W. Brown, Ed., Westerville, Ohio: American Ceramic Society, pp. 352–379, no month.

Chohayeb, A.A., et al., Evaluation of Calcium Phosphate as a Root Canal Sealer–Filler Material, *J. Endod* 13, 384–386 (Aug. 1987).

Hong, et al., (1989): The Periapical Tissue Reactions to a Calcium Phosphate Cement in the Teeth of Monkeys, *J. Dent Res* (submitted), no month.

Constantino, et al. (1989): Evaluation of a New Hydroxyapatite Cement: Cranioplasty in a Cat Model, The Fifth International Symposium on Facial Plastic Reconstructive Surgery of the Head and Neck, Toronto, Canada, no month.

De Rijk, et al. (1986): Clinical Evaluation of an Hydroxyapatite Precipitate for the Treatment of Dentinal Hypersensitivity, *Biomedical Engineering V. Recent Developments*, Proc of 5th Southern Biomedical Engineering Conference, Subrata Saha, Ed., New York: Pergamon Press, pp. 336–339, no month.

Grunninger et al, (1984): Evaluation of the Biocompatibility of a New Calcium Phosphate Setting Cement, *J. Dent Res.*, 63 (Special Issue) Abst. No. 270, no month.

Hanker et. al, (1987): Calcium Phosphate Bindrs for Hydroxyapatite Particles for Bone Reapir, *J. Dent Res.* 66, Abst. No. 1144, no month.

Sugawara, et. al, (1987): A Calcium Phosphate Root Canal Sealer–Filler, *J. Dent Res.* 66: 296 Abst. No. 1516, no month.

Sugawara et al (1989): Formation of Hydroxyapatite in Hydrogels from Tetracalcium Phosphate/Dicalcium Phosphate Mixtures, *Nihon Univ. Sch. Dent.*, vol. 31, No. 1, 372–81, 1989, no month.

Block, et al. (1988): Correction of Vertical Orbital Dystopia with a Hydroxyapatite Orbital Floor Graft, *J. Oral Maxillofac Surg* 46: 420–425, 1988, no month.

Salyer, et al. (1989): Porous Hydroxyapatite as an Onlay Bone–Graft Substituted for Maxillofacial Surgery, *Plas and Recon Surg* 84, 2:236–244, 1989, no month.

Kenney, et al. (1988): The Use of a Porous Hydroxyapatite Implant in Periodontal Defects, *J. Peridontal*, pp. 67–72 Feb. 1988, no month.

Zide et al (1987): Hydroxyapatite Cranioplasty Directly Over Dura, *J. Oral Maxillofac Surg* 45:481–486, 1987, no month.

Waite, et al. (1986): Zygomatic Augmentation with Hydroxyapatite, *J. Oral Maxillofac Surg* 44:349–352, 1986, no month.

Verwoerd, et al. (1987): Porous Hydroxyapatite–perichondrium Graft in Cricoid Reconstruction, *Acta Otolaryngol (Stockh) 1987*; 103:496–502 no month.

Grote, (1984): Tympanoplasty With Calcium Phosphate, *Arch Otolaryngology* 110:197–199, 1984, no month.

Kent, et al. (1983): Alveolar Ridge Augmentation Using Nonresorbable Hydroxyapatite With or Without Autogenous Cancellous Bone, *J. Oral Maxillofac Surg* 41:629–642, 1983, no month.

Piecuch (1986): Augmentation of the Atrophic Edentulous Ridge with Porous Replammeform Hydroxyapatite (Interpore–200), *Dental Clinics of North America* 30, 2:291–305, 1986, no month.

Misch (1987): Maxillary Sinus Augmentation for Endosteal Implants: Organized Alternative Treatment Plans, *Int J Oral Implant* 4, 2:49–58, 1987, no month.

Chow, L.C., "Calcium Phosphate Materials: Reactor Response" *Adv Dent Res* 2(1): 191–184, Aug. 1988, no month.

Fukase, et al., "Setting Reactions and Compressive Strengths of Calcium Phosphate Cements", *J Dent Res* 69(12):1852–1856, Dec. 1990, no month.

Chow, et al., "Self–Setting Calcium Phosphate Cements," Mat. Res. Soc. Symp. Proc. vol. 179, 1991, no month.

Miyazaki, et al. "Chemical Change of Hardened PCA/CPC Cements in Various Storing Solutions," *The Journal of the Japanese Soc. for Den. Mats. and Devices*, vol. 11, No. 2, 1992, no month.

Fukase et al, "Thermal Conductivity of Calcium Phosphate Cement," IADR *Abstract*, 1990, no month.

Sugawara, et al., "An In Vitro Study of Dentin Hypersensitivity Using Calcium Phosphate Cement" *Jour of Jap. Soc. for Dent. Mats & Devices*, vol. 8, No. 2 1989, no month, considered to extent of abstract.

Constantino, et al., "Hydroxyapatite Cement—Basic Chemistry and Histologic Properties," *Arch. of Otolaryngology—Head & Neck Surgery*, vol. 117, pp. 379–384 (Apr. 1991).

Freidman, et al., "Hydroxyapatite Cement—Obliteration and Reconstruction of the Cat Frontal Sinus," *Arch. of Otolaryngology—Head & Neck Surgery*, vol. 117, pp. 385–389 (Apr. 1991).

Calcium Phosphate cements: action of setting regulators on the properties of the β–tricalcium phosphate–monocalcium phosphate cements.

Mirtchi, et al., "Calcium phosphate cements: study of the β–tricalcium phosphate–monocalcium phosphate system," *Biomaterials*, vol. 10, pp. 475–480 (1989), no month.

Mirtchi, et al., "Calcium phosphate cements: study of the β–tricalcium phosphate–dicalcium phosphate–calcite cements," *Biomaterials*, vol. 11, pp. 83–88 (1990).

Mirtchi, et al., "Calcium phosphate cements: effect of fluorides on the setting and hardening of β–tricalcium phosphate–dicalcium phosphate–calcite cements," *Biomaterials*, vol. 12, pp. 505–510 (1991), no month.

Fulmer, et al. "Effects of $Na_2$ $HPO_4$ and $NaH_2PO_4$ on Hydroxyapatite Formation," *J. Biomed. Mat. Res.*, vol. 27, pp. 1095–1102 (1993), no month.

Ishikawa, et al., "The Hydrolysis of Anhydrous Dicalcium Phosphate into Hydroxyapatite," J. of Dent. Res., vol. 72, No. 2, pp. 474–480 (Feb. 1993).

Sugawara, et al., "In Vitro Evaluation of the Sealing Ability of a Calcium Phosphate Cement When Used 5s a Root Canal Sealer–Filler," J. of Endodontics, vol. 16, No. 4, pp. 162–165 (1990), no month.

Shindo, et al., "Facial Skeletal Augmentation Using Hydroxyapatite Cement," Arch. of Otolaryngology—Head & Neck Surgery, vol. 119, pp. 185–190 (Feb. 1993).

Constantino, et al., "Experimental Hydroxyapatite Cement Cranioplasty," Plastic and Reconstructive Surgery, vol. 90 No. 2, pp. 174–185 (Aug. 1992).

Sanin, et al., K. Ishikawa, S. Takagi, L.C. Chow and E.D. Eanes, "Effects of Additives on Setting Reaction of Calcium Phosphate Cement," IADR Abstr. #666 J. Dent Res. 71 189 (1992), no month.

Driessens, et al., (1993) "New Apatite Calcium Phosphate Bone Cement: Preliminary Results," in Bioceramics (Ducheyne & Christiansen, eds.) Butterworth–Heinemann Ltd., vol. 6, pp. 469–473, no month.

Miyazaki, et al., (1993) "Polymeric calcium phosphae cements: analysis of reaction products and properties," Dent.Mater. 9:41–45, no month.

Miyazaki et al,(1993) "Polymeric calcium phosphate cements: setting reaction modifiers," Dent Mater. 9:46–50, no month.

Chow et al., (1994) "Formulation of Hydroxyapatite in Cement Systems," in Hydroxyapatite and Related Materials (Brown & Constanz, eds.), CRC Press: Boca Raton, FL pp. 127–137, no month.

Constantz, et al., (1995) "Skeletal Repair by Situ Formation of the Mineral Phase of Bone," Science 267: 1796–1798, no month.

Chow and Takagi, (1995) "Rate of Dissolution of Calcium Phosphate Cements," J. Dent. Res. 74:537 (IADR Abstract #1094), no month.

Takagi and Chow, (1995) "Formation of Macropores in Calcium Phosphate Cement Implants," J. Dent. Res. 74:537 (IADR Abstract #1272), no month.

Horioglu, et al., (1995) "Composite Implant of Hydroxyapatite Cement/Osteogenic Protein–1 In Experimental Cranial Construction: Preliminary Results," Transactions of the 21st Annual Meeting for the Society for Biomaterials, San Francisco, Ca, Mar. 18–22, p. 72, no month.

Driessens, et al., (1995) "Effective formulations for the preparation of calcium phosphate bone cements," J. Mater. Sci.:Mater.Med. 5:164–170, no month.

Fernandez, et al., (1994) "Common Ion Effect on some Calcium Phosphate Cements," Clinical Mater.16:99–103, no month.

Matsuya, et al., (1994) Formation of Hydroxyapatiten a Polymeric Calcium Phosphate Cement, Proc. Int. Conf. Comp. Eng, no month.

Bermudez, et al., Optimization of Calcium Orthophosphae Cement formulation occurring in the combination of monocalcium phosphate monohydrate with calcium oxide, J. Mater.SciMater Med 5:67–71 (1994), no month.

Dickens–Venz, et. al., (1994) "Physical and chemical properties of resin–reinforced calcium phosphate cements," Dent.Mater.10:100–106, no month.

LeGeros,. et al., "Apatitic Calcium Phosphates: Possible Dental Restorative Materials", IADR Abstract No. 1482 J. Dent Res. (1982), no month.

"NASA and Dentistry" (1977), no month.

Chow, "Development of Self–Setting Calcium Phosphate Cements," Journal of the Ceramic Society of Japan 99[10] 954–964 (1991), no month.

Sugawara, et al., "Biocompatibility and Osteoconductivity of Calcium Phosphate Cement" IADR Abstract (1990), no month.

Miyazaki et al., "Polymeric Calcium Phosphate Cements", IADR Abstract (1990), no month.

Sugawara et al., "Histopathological Reactions of a Calcium Phosphate Cement Root Canal Filler", IADR Abstract (1991), no month.

Sanin et al., "Particle Size Effects on pH and Strength of Caclium Phosphate Cement", IADR Abstract (1991), no month.

Link et al., "Composite of Calcium Phosphate Cement and Genetically Engineered Protein Bioadhesive", IADR Abstract (1991), no month.

Matsuya et al., "Effects of pH on the Reactions of Tetracalcium Phosphate and Dicalcium Phosphate", IADR Abstract (1991), no month.

Chow et al., "X–ray Diffraction and Electron Microscopic Characterization of Calcium Phosphate Cement Setting Reactions", IADR Abstract (1987), no month.

Sugarawa et al., "An In Vitro Study of Dentin Hypersensitivity Using Calcium Phosphate Cement", Jour of Jap. Soc. For Dent. Mats & Devices, vol. 8, No. 2 (1989), no month, considered to extent of abstract.

Mirtchi et al., "Calcium Phosphate Cements: Action of Setting Regulars on the Properties of the β–tricalcium Phosphate–Monocalcium Phosphate Cements" Biomaterials, vol. 10, pp. 634–638 (1989).

Cherng et al., (1995) Effects of Gelling Agents on Calcium Phosphate Cements, J. Dent. Res. 74:242 (IADR Abstract, No. 1845).

Horioglu et al., (1999) "Long–Term Follow–Up of Hydroxyapatite Cement (HAC) Implant for Craniofacial Construction", Transactions of the 21$^{st}$ Annual Meeting for the Society of Biomaterials, San Francisco, CA, Mar. 18–22, p. 198, no month available.

Fujikawa et al., (1999) "Histopathological Reaction of Calcium Phosphate Cement in Periodontal Bone Defect", Dent. Mater. J. 10:45–57, no month available.

Sugawara et al., (1995) "Histopathological Reaction of Calcium Phosphate Cement Root Canal Filler", J. Hard Tissue Biology, 4:1–7, no month available.

Shors et al., "Porous Hydroxyapatite", An Introduction to Bioceramics, pp. 181–198, no date.

Fukase et al., "Setting Reactions and Compressive Strengths of Calcium Phosphate Cements", J Dent Res 69 (12): 1852, Dec., (1990), no month available.

Mutsuya et al., Effect of Fluoride on Apatite Formation From $Ca_4(PO_4)_2O$ in 0.1 mol L$^{-1}$ $KH_2PO_4$, J Mat Sci: Materilas in Medicine 9 (1998) pp. 325–331, no month available.

Chang et al., "Osteoconduction of Porous Hydroxyapatite with Various Pore Configurations", Biomaterials 21 (2000) 1291–1298, no month available.

Chow et al., "Calcium Phosphate Cements", Cements Research Progress, (1999) pp. 215–238, no month available.

Xu et al., "Calcium Phosphate Cement Containing Resorbable Fibers for Short Term Reinforcement and Macroporosity", Biomaterials 0 (2001) 1–10, no month available.

Xu et al., "Strong and Macroporous Calcium Phosphate Cement: Effects of Porosity and Fiber Reinforcemen on Mechanical Properties", *Macroporous Calcium Phosphate Cement*, pp. 1–10, no month available.

Chow, "Calcium Phosphate Cements: Chemistry, Properties and Applications", *Mat. Res. Soc. Sump. Proc.*, vol. 599 (2000), no month available.

Takagi et al., Formation of Macropores in Calcium Phosphate Cement Implants, *J. Mat. Sci: Materials in Medicine*, 12 (2001) 135–139, no month.

Von Gonten et al., "Load–Bearing Behavior of a Simulated Craniofacial Structure Fabricated From a Hydroxyapatite Cement and Bioresorbable Fiber–Mesh" *J. Mater. Sci.: Materials in Medicine*, 11 (2000) 95–100, no month.

Xu et al., "Effects of Fiber Length and Volume Fraction on the Reinforcement of Calcium Phosphate Cement", *J. Mater. Sci: Materials in Medicine*, 12 (2001) 57–65, no month.

Xu et al., "Reinforcement of a Self–Setting Calcium Phosphate Cement with Different Fibers", *Journal o Biomedical Materials Research*, Oct. 2000, vol. 51, No. 1, pp. 107–114.

Suchanek et al., "Processing and Properties of Hydroxyapatite–Based Biomaterials for use as Hard Tissu Replacement Implants", *J. Mater. Res.*, vol. 13, No. 1, Jan. 1998, pp. 94–117.

Simske, et al., "Porous Materials for Bone Engineering", *Materials Science Forum*, vol. 250 (1997) pp. 151–182, no month.

LeGeros, "Biodegradation and Bioresorption of Calcium Phosphate Ceramics", *Clinical Materials*, 14 (1993) pp. 65–88, no month.

Friedman et al., "BoneSource Hydroxyapatite Cement: A Novel Biomaterial for Craniofacial Skeletal Tissu Engineering and Reconstruction", *Hac For Tissue Engineering and Reconstruction*, pp. 428–432, no date.

Takagi, et al., "Morphological and Phase Characterizations of Retrieved Calcium Phosphate Cement Implants", pp. 36–41 (2001), no month.

Ishikawa et al., "Reaction of Calcium Phosphate Cements With Different Amounts of Tetracalcium Phosphate and Dicalcium Phosphate Anhydrous", *CPC With Different TTCP/DCPA Molar Ratios*, pp. 504–510 (1999), no month.

Miyamoto et al., "Histological and Compositional Evaluations of Three Types of Calcium Phosphate Cements When Implanting in Subcutaneous Tissue Immediately After Mixing", *Three CPCs in Soft Tissue*, 1999, pp. 36–42 (1999), no month.

Constantz et al., "Histological, Chemical, and Crystallographic Analysis of Four Calcium Phosphate Cement in Different Rabbit Osseous Sites", *Calcium Phosphate Cements*, 1998, pp. 451–461 (1998), no month.

Ginebra et al., "Setting Reaction and Hardening of an Apatitic Calcium Phosphate Cement", *J. Dent. Res.*, 76 (4): 905–912, Apr. 1997.

English Translation, Japanese Examiner's Citation to References, Feb. 2, 1999.

Australian Examiner's Citation to References, Sep. 20, 1996.

Blumenthal, et al., "Effect of Preparation Conditions on the Properties and Transformation of Amorphous Calcium Phosphate", *Mat. Res. Bull.* 7:1181–1190 (1972), no month.

Aboba, "X–Ray Diffraction Study on the Amorphous and Crystalline Components in Bone Mineral", *Chem Abstracts*, vol. 91, No. 13 Abstract No. 105935r, (1979), no month.

Aboba et al., "Small Angle X–Ray Scattering Study on the Transformation of Amorphous Calcium Phosphate to Crystalline Apatite," *Chem. Abstracts*, vol. 91, No. 13, Abstract No. 105934q (1979), no month.

Tung et al., "Hydrolysis of Dicalcium Phosphate Dihydrate in the Presence or Absence of Calcium Fluoride", Basic Biological Sciences *Dent. J. Res.* 64(1):2–5 Jan. 1985.

Tung et al., "An Intermediate State in Hydrolysis of Amorphous Calcium Phosphate", Calcified Tissue International, 783–790 (1983), no month.

Tung, et al., "The Effects of Calcium Phosphate Solutions on Permeability of Dentin" *J. Dent. Res.*, 65 Abstract No. 167 (1986), no month.

Tung et al., "Effects of Calcium Phosphate Solutions on Dentin Permeability", vol. 19, No. 8 *J o Endodontic* (1983), no month.

Trautz, "Crystallographic Studies of Calcium Carbonate phosphate" Annals of the N.Y. Acad. Sci. 35 Article 1: 145–160 (1960), no month.

Termine et al., "Calcium Phosphate in vitro", *Chem. Abstracts*, vol. 73, Abstract No. 126985a, (1970), no month.

Yasue et al, "Synthesis and Characteristics of Amorphous Calcium Carbonate in Ethanol", *Fac. Sci Eng. Nihon Univ. Gypsum Lime*, (1985) 198 245–52 Japan, no month.

Bowen et al., "Development of an Adhesive Bonding System", *Operative Dentistry*, Supplement 5 (1992) pp 75–80, no month.

Yu et al., "Self–Setting Hydroxyapatite Cement: A Novel Skeletal Drug–Delivery System for Antibiotic", *J Pharm. Sci.*, vol. 81, No. 6, Jun. 1992, pp. 529–531.

de Groot, "Ceramics of Calcium Phosphates: Preparation and Properties", *Bioceramics of Calcium Phosphate*, pp. 99–114, no date.

Posner et al. "Synthetic Amorphous Calcium Phosphate and Its Relation to Bone Mineral Structure" *Accounts of Chemical Research*, 8, 273 (1975), no month.

Zimmerman et al., "The Effect of Remineralization Fluids on Carious Lesions in Vitro", IADR Abstract No. 282 (1979), no month.

PREMIXED CALCIUM PHOSPHATE CEMENT PASTES

CROSS REFERENCE TO RELATED APPLICATION

This is a utility application based upon provisional application Serial No. 60/263,894 filed Jan. 24, 2001 entitled "Premixed Calcium Phosphate Cement Pastes" for which priority is claimed.

BACKGROUND OF THE INVENTION

This development was supported in part by USPHS Research Grant DE11789 to the American Dental Association Health Foundation from the NIDCR. The United States or an agency thereof may therefor have certain rights to the claimed invention.

A self-hardening calcium phosphate cement, consisting of tetracalcium phosphate (TTCP) and anhydrous dicalcium phosphate has been shown in clinical studies to be efficacious as a bone repair material. The hardening time (HT) of the cement is about 30 minutes when the powder constituents are mixed with water and 5 minutes when mixed with a phosphate solution as the liquid. Hydroxyapatite (HA) is the major product formed as a result of the mixing and hardening. In recent years, additional calcium phosphate cements (CPC) that do not contain TTCP have been developed, e.g. α-tricalcium phosphate (TCP) and $CaCO_3$; dicalcium phosphate (DCPA) and $Ca(OH)_2$. These cements harden in 10 minutes when mixed with a phosphate solution, and they also form HA as the final product.

A cement paste of the type referenced mixed with glycerol was studied for root canal filling, sealing, and injectability and it was reported that the glycerol-calcium phosphate cement (CPC) paste showed better biocompatibility than a number of presently used root canal filling or sealing materials. However, the prior art did not teach a paste material useful as a bone cement that remains stable over a period of time and hardens only when delivered to a desired site.

SUMMARY OF THE INVENTION

The present invention comprises compositions and means for formulating premixed glycerol and calcium phosphate cement pastes that are stable in a package, resist washout, and will harden only after being delivered to the defect or implant site. Glycerol was used as the liquid because the CPC hardening reaction to form HA does not occur in a water-free environment. Hydroxypropyl methylcellulose (HMC) and $Na_2HPO_4$ were also added to improve the paste cohesiveness and accelerate cement hardening upon delivery to a desired repair site.

DESCRIPTION OF THE PREFERRED EMBODIMENT

TTCP was prepared by heating an equimolar mixture of commercially obtained DCPA and $CaCO_3$ at 1500° C. for six hours in a furnace and then quenched in air or inert gas to room temperature. Also, TCP was prepared by heating a mixture that contained 2 mol of DCPA and 1 mol of $CaCO_3$ to 1200° C. for six hours followed by quenching to room temperature. The powders used were ground individually in a planetary ball mill in cyclohexane, ethanol, or dry to obtain the desired median particle size which is about 15 microns and as disclosed in the prior art for making CPC powders.

Nine liquids containing glycerol and various amounts of HMC (in powder form) and $Na_2HPO_4$ (in powder form) were then prepared. Their compositions, expressed as mass fractions (%) of HMC and $Na_2HPO_4$, are shown in Table 1. The CPC-I, -II and -III were an equimolar mixture of (1) TTCP and DCPA; (2) α-TCP and $CaCO_3$, and (3) DCPA and $Ca(OH)_2$, respectively. CPC pastes were prepared by mixing the prepared CPC powder with the liquid glycerol mixture at powder-to-liquid ratios of 3.5 to 1 to 1.8 to 2.2 and 1.5 to 1.8, respectively. Diametral tensile strength (DTS) samples were prepared by placing the paste into molds (6 mm diameter×3 mm height) with ≈2 $MP_a$ of pressure applied. The DTS samples were kept in a mold covered with two fritted glass slides and immersed in a physiologic-like solution (PLS) [1.15 mM Ca, 1.2 mM P, 133 mM NaCl, 50 HEPES, pH=7.4] at 37° C. Glycerol-PLS exchange occurred through the fritted glass allowing the CPC to harden. Samples were removed at 4 hours, then immersed in PLS for an additional 20 h. A Universal Testing Machine (United Calibration Corp, Garden Grove, Calif., USA) measured DTD values at a loading rate of 10 mm/min. The Gilmore needle method measured HT. Powder X-ray diffraction analysis (XRD) determined the extent of CPC conversion to HA.

All pastes had excellent washout resistance, they remained stable and hardened while immersed in PLS. The HT and the DTS of 24 hour samples are shown in Table 1. The Newman-Kuels multiple comparison test indicated that the $Na_2HPO_4$ amount, not the HMC amount, significantly ($P<0.05$) affected the DTS and HT. Within each group of HMC amount for CPC-I, the lowest phosphate amount substantially increased the DTS while the highest phosphate amount dramatically reduced the HT. For samples CPC-II and -III, the highest phosphate amount significantly increased the DTS and decreased the HT. X-ray diffraction showed only partial conversion of CPC-I to HA and complete conversions of CPC-II and -III to HA in the 24 hour samples.

TABLE 1

Na2NPO4 and HMC compositions expressed as mass fraction (%) in glycerol, 24 h DTS and HT.

| Liquid | Na₂NPO4 | HMC  | DTS (MPa) | HT (Min) |
|--------|---------|------|-----------|----------|
| CPC-I  |         |      |           |          |
| L1     | 7.5     | 0.55 | 4.1 (0.4) | 111 (6)  |
| L2     | 15      | 0.55 | 2.8 (0.2) | 93 (3)   |
| L3     | 30      | 0.55 | 2.1 (0.2) | 62 (2)   |
| L4     | 7.5     | 1.1  | 4.2 (0.2) | 97 (8)   |
| L5     | 15      | 1.1  | 2.6 (0.1) | 92 (3)   |
| L6     | 30      | 1.1  | 2.6 (0.3) | 63 (3)   |
| L7     | 7.5     | 2.2  | 3.6 (0.6) | 97 (6)   |
| L8     | 15      | 2.2  | 3.2 (0.3) | 93 (3)   |
| L9     | 30      | 2.2  | 2.3 (0.3) | 62 (3)   |
| CPC-II |         |      |           |          |
| L1     | 7.5     | 0.55 | 2.0 (0.4) | 117 (3)  |
| L2     | 15      | 0.55 | 2.5 (0.2) | 107 (3)  |
| L3     | 30      | 0.55 | 3.4 (0.4) | 80 (5)   |
| CPC-III|         |      |           |          |
| L1     | 7.5     | 0.55 | 0*        | >420     |
| L2     | 15      | 0.55 | 1.0 (0.2) | 170 (5)  |
| L3     | 30      | 0.55 | 1.5 (0.1) | 125 (5)  |

Numbers in parentheses denote standard uncertainty (n = 4 and 3 for DTS and HT, respectively).
*Not measurable.

The premixed CPC pastes would generally have a longer hardening time and lower physical strength, but the results suggest that cement pastes with excellent washout resistance can be prepared by incorporating HMC and $Na_2HPO_4$ in glycerol. Phosphate generally decreased HT and DTS for CPC-I, and increased DTS for CPC-II and -III. HMC appeared to decrease HA formation for CPC-I, but had no effect for CPC-II and -III, and did not affect DTS.

In sum, formation of a bone replacement or dental replacement paste results by combining dry powder constituents, characterized by their conversion to HA in the presence of water or phosphate solutions, with glycerol and hydroxypropyl methyl cellulose and/or $Na_2HPO_4$. The ratio of combined constituents is broad and the resulting paste can be formulated to control rather precisely, the hardening times. Glycerol compounds, analogs and substitutes as well as cellulose analogs and substitutes are within the scope of the invention.

What is claimed is:

1. A composition of matter for dental restoration and bone implants and restoration comprising, in combination:
    a mixture of liquid glycerol and a powdered calcium phosphate compound selected from the group consisting of tetracalcium phosphate; anhydrous dicalcium phosphate; α-tricalcium phosphate with calcium carbonate; dicalcium phosphate with calcium hydroxide and mixtures thereof, said mixture being free of water and in the form of a paste.

2. The composition of claim 1 including a cellulose compound.

3. The composition of claim 1 including hydroxypropyl methylcellulose.

4. The composition of claim 1 including $Na_2HPO_4$.

5. The composition of claim 1 including an accelerator.

6. The composition of claim 1 comprising a water free paste comprised of a liquid including glycerol, hydroxypropyl methlycellulose and $Na_2HPO_4$ and powdered tetracalcium phosphate prepared from dicalcium phosphate and calcium carbonate.

7. A paste for bone and tooth restoration comprising, in combination:
    a water free mixture of liquid glycerol and powdered tetracalcium phosphate prepared from dicalcium phosphate and calcium carbonate.

8. The paste of claim 7 wherein the liquid further includes hydroxy methylcellulose.

9. The paste of claim 7 wherein the liquid further includes $Na_2NPO_4$.

10. The paste of claim 8 wherein the mass ratio of powder to liquid is in the range of 3.5 to 1 to 1.5 to 1.8.

* * * * *